United States Patent
Drmanovic (10) Patent No.: US 10,610,676 B2
(45) Date of Patent: Apr. 7, 2020

(54) DISINFECTING LUER CONNECTOR (71) Applicant: Zoran Drmanovic, Palm City, FL (US)

(72) Inventor: Zoran Drmanovic, Palm City, FL (US)

(73) Assignee: DRMA Group International LLC, Palm City, FL (US)

( * ) Notice: Subject to any disclaimer, the term of this patent is extended or adjusted under 35 U.S.C. 154(b) by 113 days.

(21) Appl. No.: 15/275,518

(22) Filed: Sep. 26, 2016

(65) Prior Publication Data

US 2018/0085568 A1    Mar. 29, 2018

(51) Int. Cl.
*A61M 39/16* (2006.01)
*A61M 39/20* (2006.01)

(52) U.S. Cl.
CPC .......... *A61M 39/162* (2013.01); *A61M 39/20* (2013.01)

(58) Field of Classification Search
CPC .. A61M 39/16; A61M 39/162; A61M 39/165; A61M 39/20; A61M 39/18; A61M 5/002; A61M 2005/3104; A61M 2005/3106; A61M 2005/3117; A61M 2005/3118; A61M 2039/0288
USPC ....................................................... 604/265
See application file for complete search history.

(56) References Cited

U.S. PATENT DOCUMENTS

| | | | |
|---|---|---|---|
| 2,400,722 A | 5/1946 | Swan | |
| 4,340,052 A | 7/1982 | Dennehey et al. | |
| 4,440,207 A | 4/1984 | Genatempo et al. | |
| 4,610,469 A * | 9/1986 | Wolff-Mooij | A61M 39/045 251/149.1 |
| 5,053,003 A | 10/1991 | Dadson et al. | |
| 5,242,425 A | 9/1993 | White et al. | |
| 5,295,975 A | 3/1994 | Lockwood, Jr. | |
| 5,324,264 A | 6/1994 | Whitaker | |
| 5,429,612 A | 7/1995 | Berthier | |
| 5,681,283 A | 10/1997 | Brownfield | |
| 5,792,120 A | 8/1998 | Menyhay | |
| 5,885,249 A | 3/1999 | Irisawa | |
| 6,045,539 A | 4/2000 | Menyhay | |

(Continued)

FOREIGN PATENT DOCUMENTS

| EP | 0409180 A1 | 1/1991 |
|---|---|---|
| EP | 0520930 A1 | 12/1992 |

(Continued)

*Primary Examiner* — Kami A Bosworth
*Assistant Examiner* — Leah J Swanson
(74) *Attorney, Agent, or Firm* — Dmitry Zuev, Esq.

(57) ABSTRACT

An assembly for disinfecting a female port of a medical implement is provided. The assembly includes a receiving portion and a disinfecting member disposed substantially inside the receiving portion. The receiving portion includes an open proximal end, a side wall, and a syringe tip having an external surface. An internal surface has a plurality of protrusions disposed near the open proximal end. The syringe tip includes a passageway therethrough in a fluid communication with the chamber and an external surface extending towards the open proximal end so as to create a cavity between the internal surface of the side wall and the external surface of the syringe tip. The protrusions are shaped to engage helical threads of the female port of a medical implement. The second disinfecting member is disposed substantially inside the cavity created by the protrusions of the internal surface and the external surface of the syringe tip.

17 Claims, 9 Drawing Sheets

(56) References Cited

U.S. PATENT DOCUMENTS

| | | |
|---|---|---|
| 6,171,287 B1 * | 1/2001 | Lynn .................... A61M 39/02 251/149 |
| 6,322,540 B1 | 11/2001 | Grabis et al. |
| 6,391,003 B1 | 5/2002 | Lesch, Jr. |
| 6,409,706 B1 | 6/2002 | Loy |
| 6,547,764 B2 | 4/2003 | Larsen et al. |
| 6,582,408 B1 | 6/2003 | Buch-Rasmussen et al. |
| 6,908,460 B2 | 6/2005 | Distefano |
| 7,682,561 B2 | 3/2010 | Davis et al. |
| 7,815,611 B2 | 10/2010 | Giambattista et al. |
| 7,931,877 B2 | 4/2011 | Steffens et al. |
| 8,065,773 B2 | 11/2011 | Vaillancourt et al. |
| 8,069,523 B2 | 12/2011 | Vaillancourt et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,231,587 B2 | 7/2012 | Solomon et al. |
| 8,298,196 B1 | 10/2012 | Mansour |
| 8,328,767 B2 | 12/2012 | Solomon et al. |
| 8,336,151 B2 | 12/2012 | Kerr et al. |
| 8,336,152 B2 | 12/2012 | Vaillancourt et al. |
| 8,343,112 B2 | 1/2013 | Solomon et al. |
| 8,491,546 B2 | 7/2013 | Hoang et al. |
| 8,523,830 B2 | 9/2013 | Solomon et al. |
| 8,523,831 B2 | 9/2013 | Solomon et al. |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,671,496 B2 | 3/2014 | Vaillancourt et al. |
| 8,696,820 B2 | 4/2014 | Vaillancourt et al. |
| 8,734,384 B2 | 5/2014 | Boyd et al. |
| 8,740,864 B2 | 6/2014 | Hoang et al. |
| 8,784,388 B2 | 7/2014 | Charles et al. |
| 8,961,475 B2 | 2/2015 | Solomon et al. |
| 8,999,073 B2 | 4/2015 | Rogers et al. |
| 9,039,989 B2 | 5/2015 | Liu et al. |
| 9,079,692 B2 | 7/2015 | Solomon et al. |
| 9,114,915 B2 | 8/2015 | Solomon et al. |
| 9,186,707 B2 | 11/2015 | Vaillancourt et al. |
| 9,192,449 B2 | 11/2015 | Kerr et al. |
| 9,259,284 B2 | 2/2016 | Rogers et al. |
| 9,283,367 B2 | 3/2016 | Hoang et al. |
| 9,283,368 B2 | 3/2016 | Hoang et al. |
| 9,283,369 B2 | 3/2016 | Ma et al. |
| 2006/0189961 A1 * | 8/2006 | Miyahara ............... A61M 39/14 604/535 |
| 2008/0097407 A1 * | 4/2008 | Plishka ............... A61M 39/045 604/533 |
| 2008/0177250 A1 | 7/2008 | Howlett et al. |
| 2009/0137969 A1 | 5/2009 | Colantonio et al. |
| 2009/0307449 A1 | 12/2009 | Prahlad et al. |
| 2010/0272379 A1 | 10/2010 | Hu et al. |
| 2011/0054440 A1 * | 3/2011 | Lewis ................... A61M 39/16 604/506 |
| 2012/0016318 A1 | 1/2012 | Hoang et al. |
| 2012/0302970 A1 | 11/2012 | Tennican |
| 2013/0171030 A1 * | 7/2013 | Ferlic ................... A61M 39/20 422/119 |
| 2015/0360021 A1 | 12/2015 | Limdico et al. |
| 2017/0232121 A1 | 8/2017 | Chiu et al. |
| 2018/0064604 A1 | 3/2018 | Drmanovic |
| 2018/0071508 A1 | 3/2018 | Drmanovic |

FOREIGN PATENT DOCUMENTS

| | | |
|---|---|---|
| EP | 0832661 A2 | 4/1998 |
| EP | 1336419 A1 | 8/2003 |
| WO | 2015120336 A1 | 8/2015 |

* cited by examiner

Fig. 11B

DISINFECTING LUER CONNECTOR

BACKGROUND

The present invention generally relates to a disinfecting connector device, and more specifically, to a device for disinfecting a female port of a medical implement.

The presence of intravenous catheters is the major risk factor for the development of bloodstream infections. These catheters can be either central or peripheral. Most of the catheters have female luer threads at their proximal end. Needleless hub connectors are ordinarily used at the end of these catheters as an injection port and to prevent blood from coming out of the catheter when it is not in use. The hub connectors contain a female luer lock disposed at their proximal end. A syringe having male luer threads is used to inject fluids or medication. Needless hub connectors also have male luer threads at their distal end. They are used to connect the distal end with the female luer threads of the intravenous catheters.

Various infections can be introduced at any connection spot as a result of using dirty syringe tips having male luer threads, or contaminated fluid or medication inside the syringe. Female luer threads located on the hub or intravenous catheter and the hub's injection membrane can also be contaminated. Syringes come to the hospital in sterile, sealed packages. Once a medical professional opens the package, the syringe is exposed to potential contamination. Usually, a needle is attached to the syringe tip, which is used to protect the tip and to draw medication from a vial into the syringe. When the needle is separated from the syringe, it may be placed on a potentially contaminated surface, and the syringe may be used to inject medication into the intravenous catheter by using a needleless hub. After that, the syringe may also be placed on the same contaminated surface instead of being connected back to the needle. This creates an opportunity for contamination of both the syringe and the needle. In addition, penetration of the contaminated vial's rubber stopper with the needle can introduce contamination inside the syringe, and later, into the bloodstream.

Attempts have been made to disinfect connection spots. However, there remains a need for a convenient and reliable disinfecting luer connector that would guarantee 100% compliance of medical professionals with antiseptic techniques.

SUMMARY

An embodiment provides an assembly for disinfecting a female port of a medical implement. The assembly includes a receiving portion and a disinfecting member disposed substantially inside the receiving portion. The receiving portion includes an open proximal end, a side wall, and a syringe tip. The side wall includes an internal surface defining a chamber for retaining a fluid into which the female port of the medical device is received. The internal surface has a plurality of protrusions disposed near the open proximal end, wherein the protrusions are shaped to engage helical threads of the female port of a medical implement. The syringe tip includes a passageway therethrough in a fluid communication with the chamber. The syringe tip further includes an external surface extending towards the open proximal end of the receiving portion of the assembly so as to create a cavity between the internal surface of the side wall and the external surface of the syringe tip. The disinfecting member is disposed near the open proximal end of the receiving portion in a direction substantially perpendicular to the internal surface of the side wall so as to completely cover the open proximal end. The disinfecting member has an opening to receive the female port of the medical implement. The disinfecting member is disposed substantially inside the cavity created by the protrusions of the internal surface of the side wall and the external surface of the syringe tip.

The assembly may further include an additional disinfecting member disposed near the open proximal end of the receiving portion in a direction substantially perpendicular to the internal surface of the side wall so as to completely cover the open proximal end. The additional disinfecting member may include an opening to receive the female port of the medical implement.

The disinfecting member may be attached to the external surface of the syringe tip. Alternatively, the disinfecting member may be attached to the internal surface of the side wall. The disinfecting member and the additional disinfecting member may be impregnated with a disinfecting agent. The additional disinfecting member may be attached to an internal surface of the side wall of the receiving portion of the assembly.

The disinfecting member and/or the additional disinfecting member may compress upon contact with the female port of the medical implement to release a disinfecting agent. The disinfecting member and/or the additional disinfecting member may subsequently return to its original shape when the female port of the medical implement no longer contacts the disinfecting member and/or the additional disinfecting member.

The female port of a medical implement may include a membrane. Upon contact with the membrane, the disinfecting member and/or the additional disinfecting member may release a disinfecting agent onto the membrane.

The receiving portion may further include a secondary side wall disposed between the internal surface of the side wall and the external surface of the syringe tip. The syringe tip may be disposed completely inside the chamber. In another embodiment, a portion of the syringe tip may be disposed outside the chamber.

The opening in the additional disinfecting member may be a single line opening or an opening formed by two substantially perpendicular lines.

The medical implement may be a needleless hub connector, a triple lumen catheter, or an intravenous needle.

The assembly further includes a protecting member disposed outside the proximal end of the receiving portion and in full contact with that end so as to protect the disinfecting member when the assembly is not in use. The protecting member may include a metal foil or a plastic film.

In another embodiment, the protecting member may be a cap having a housing for covering the proximal end of the receiving portion of the assembly. The housing may have an opening and a cavity including a surface. The protecting member may further include a disinfecting pad disposed within the cavity and attached to the surface thereof to protect and disinfect the proximal end of the receiving portion of the assembly.

Another embodiment provides a method for disinfecting a female port of a medical implement. The method includes providing an assembly for disinfecting a female port of a medical implement. The assembly includes a receiving portion and a disinfecting member disposed substantially inside the receiving portion. The receiving portion includes an open proximal end, a side wall, and a syringe tip. The side wall includes an internal surface defining a chamber for retaining a fluid into which the female port of the medical device is received. The internal surface has a plurality of protrusions disposed near the open proximal end, wherein the protrusions are shaped to engage helical threads of the female port of a medical implement. The syringe tip includes a passageway therethrough in a fluid communication with the chamber. The syringe tip further includes an external surface extending towards the open proximal end of the receiving portion of the assembly so as to create a cavity between the internal surface of the side wall and the external surface of the syringe tip. The disinfecting member is disposed near the open proximal end of the receiving portion in a direction substantially perpendicular to the internal surface of the side wall so as to completely cover the open proximal end. The disinfecting member has an opening to receive the female port of the medical implement. The disinfecting member is disposed substantially inside the cavity created by the protrusions of the internal surface of the side wall and the external surface of the syringe tip. The method further includes inserting the medical implement through the opening in the first disinfecting member inside the receiving portion of the assembly and connecting the female port of the medical implement by engaging the helical threads of the female port with the protrusions of the internal surface of the side wall.

The receiving portion may further include an additional disinfecting member disposed near the open proximal end of the receiving portion in a direction substantially perpendicular to the internal surface of the side wall so as to completely cover the open proximal end. The additional disinfecting member may include an opening to receive the female port of the medical implement.

The method may further include injecting a fluid through the female port of the medical implement into the receiving portion of the assembly. The female port of the medical implement may then be disconnected from the receiving portion of the assembly by disengaging the helical threads of the female port from the protrusions of the internal surface of the side wall. The medical implement may then be removed from the receiving portion of the assembly, and the open proximal end of the receiving portion may then be capped with a protective member.

BRIEF DESCRIPTION OF THE DRAWINGS

The above and other aspects and features of the present disclosure will become more apparent by describing in detail exemplary embodiments thereof with reference to the attached drawings, in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below by referring to the figures to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross-section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"Substantially" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "substantially" can mean within one or more standard deviations, or within ±30%, 20%, 10%, 5% of the stated value.

An embodiment provides an assembly for disinfecting a female port of a medical implement. The assembly includes a receiving portion and a disinfecting member disposed substantially inside the receiving portion. The receiving portion includes an open proximal end, a side wall, and a syringe tip. The side wall includes an internal surface defining a chamber for retaining a fluid into which the female port of the medical device is received. The internal surface has a plurality of protrusions disposed near the open proximal end, wherein the protrusions are shaped to engage helical threads of the female port of a medical implement. The syringe tip includes a passageway therethrough in a fluid communication with the chamber. The syringe tip further includes an external surface extending towards the open proximal end of the receiving portion of the assembly so as to create a cavity between the internal surface of the side wall and the external surface of the syringe tip. The disinfecting member is disposed near the open proximal end of the receiving portion in a direction substantially perpendicular to the internal surface of the side wall so as to completely cover the open proximal end. The disinfecting member has an opening to receive the female port of the medical implement. The disinfecting member is disposed substantially inside the cavity created by the protrusions of the internal surface of the side wall and the external surface of the syringe tip.

The assembly may further include an additional disinfecting member disposed near the open proximal end of the receiving portion in a direction substantially perpendicular to the internal surface of the side wall so as to completely cover the open proximal end. The additional disinfecting member may include an opening to receive the female port of the medical implement.

As stated above, current male luer connectors found on most syringes, needleless hubs, and other devices do not have any disinfecting properties. The same is true for luer slip connectors found on luer slip syringes. These connection sites are easily contaminated and various infections may be introduced into the bloodstream. All present male luer connectors have a chamber which is shorter than the tip of the connector. During the connection process, the tip enters either the needleless hub or intravenous catheter directly. Once a substantial portion of the tip is introduced, complementary threads make a connection, and the device is ready for injection of medications or withdrawal of blood. A luer slip connector does not have a chamber, so the tip of the syringe enters the hub or intravenous catheter to form a connection. Before both of these types of connections are made, a medical professional is expected to use an alcohol swab to clean the injection membrane of the needleless hub. Occasionally, a SwabCap®, which is a disinfecting cap, can be used to cover the needleless connector and to protect it from touch and airborne contamination. When SwabCap® is present, it has to be removed. However, even this would not prevent bloodstream infection when the tip of the luer connector and its threads are contaminated.

The purpose of the present invention is to create a new type of a luer connector which would include a chamber and two disinfecting pads impregnated (soaked) with a disinfecting agent. In case of a luer lock connection, the chamber of the invention would be longer than the current luer chambers in order to completely cover the tip of the connector and allow enough space for the first disinfecting pad. In case of a slip connector, which currently lacks a chamber, a new chamber would be added. This chamber too should be long enough to cover the tip and to allow enough space for both disinfecting pads. The first disinfecting pad should completely cover the syringe's proximal end and the second disinfecting pad would be located between the male luer threads of the chamber and the syringe tip (or side wall and the tip in the case of a luer slip connector).

The first disinfecting pad has an opening (for example, a central cut) which allows the top portion of the hub to penetrate it in order to come into contact with the tip. The first disinfecting pad is soaked with the disinfecting agent to disinfect the injection membrane of the hub and its threads, as they are approaching the tip to make a connection and to allow injection of the medication. The second disinfecting pad keeps the connector's tip and its male luer threads sterile by soaking them with the disinfecting agent. After a needleless hub or an intravenous catheter penetrates the first disinfecting pad, it compresses the second disinfecting pad. This compression would cause the disinfecting agent to be released and disinfect all elements involved with this connection. After the needleless hub is disconnected a second pad would expand and absorb the extra amount of the disinfecting agent. Syringes with these new, disinfecting luer lock or luer slip connectors may come in sterile, sealed packages. The sterilization process should be chosen appropriately to avoid altering the disinfecting agent inside the connector. An outside surface of the first pad may be covered with a peelable foil to prevent evaporation and spillage of the disinfecting agent. A medical professional would peel off the foil, and the connector would be ready for its first use. After the first use, a medical provider would protect the connector's tip and the threads by connecting them to the sterile needle covered with a protective cap. Another alternative is a specially designed plastic or rubber cap that fits the chamber's diameter. This cap could be included inside the same sterile, sealed package. The cap could also contain its own disinfecting pad soaked with a disinfecting agent. Once placed on the chamber, the cap would protect it from contamination, prevent evaporation of the disinfecting agent inside the chamber, and add an extra amount of the disinfecting agent to the pad. The cap also may contain a peelable foil in order to prevent spillage and evaporation, and may be peeled off before its first use.

Use of this new type of luer connector should significantly reduce the risk of bloodstream infection and eliminate the need for scrubbing the end of the intravenous catheter or the top portion of the needleless hub with alcohol swabs before use. It would guarantee forced compliance of medical professionals with antiseptic techniques. This invention is not limited to syringes only but can also be applied to any piece of medical equipment that has a luer connector on it. One example is a needleless hub connector which contains male luer threads at its distal end, which is used to connect to the intravenous catheter's female threads. This end should also contain a longer chamber and two disinfecting pads. In general, the invention would work with any male luer connector and would disinfect many different types of medical implements. It is to be understood that variations and modifications of the present invention may be made without departing from the scope thereof.

The embodiments of the present invention will now be described in greater detail.

Figure 1:
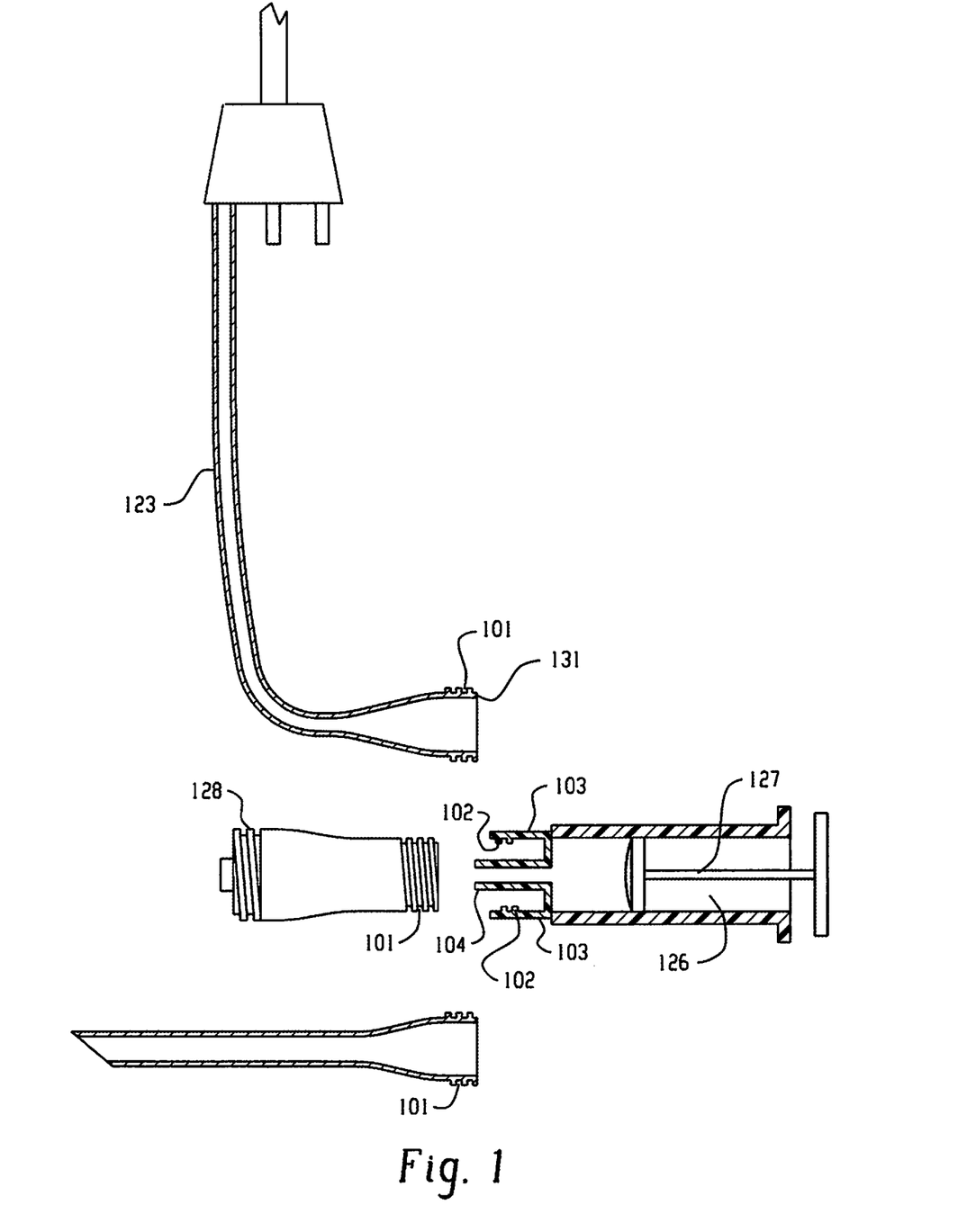
FIG. 1 shows a conventional triple lumen intravenous catheter (at the top left), a needleless hub connector (in the middle left), an intravenous needle (at the bottom left), and a syringe with a typical luer lock connector (in the middle right)

FIG. 1 illustrates various medical devices having female luer threads at their end. At the top, FIG. 1 illustrates a triple lumen catheter with only one port 123 of its three ports shown proximally, which has female luer threads 101. In the middle left, FIG. 1 illustrates a typical needleless hub connector with the female luer threads 101 located on its proximal end and male luer threads 128 disposed on its distal end. At the bottom, FIG. 1 shows a typical intravenous needle with its female luer threads 101. In the middle right, FIG. 1 shows a typical luer lock syringe having a chamber 125, male luer threads 102, a side wall 103, a syringe tip 104, a floor wall 107, a reservoir 126, and a plunger 127. This syringe can be connected to any one of these three devices with complementary female luer threads 101 and many other devices.

Figure 2:
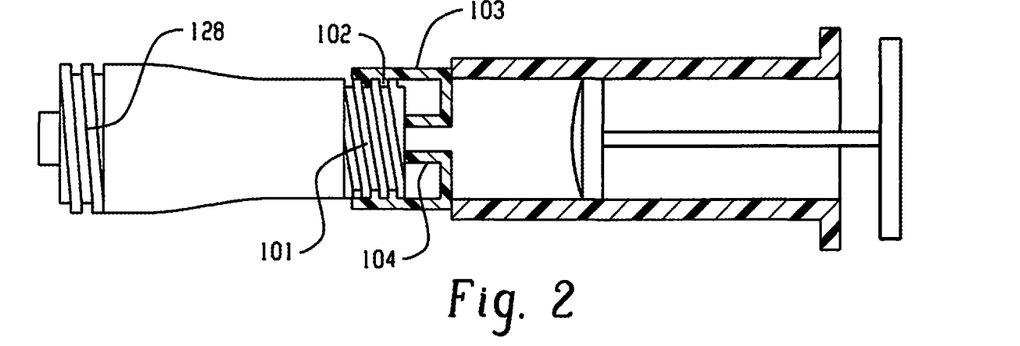
FIG. 2 shows a typical connection formed by the male luer threads of a syringe with the female luer threads of the needleless hub.

FIG. 2 shows a typical needleless hub and a typical luer lock syringe making a complete connection, which is ready for injection of the medication. The complementary male luer threads 102 connect with the female luer threads 101 located on the hub. The syringe tip 104 pushes a hub's injection membrane 110 inside and partially enters the hub.

Figure 3A:
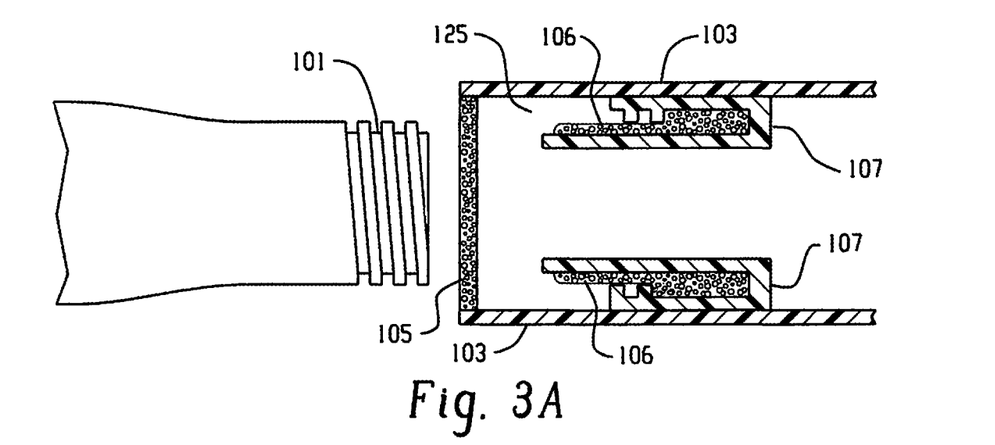
FIG. 3A shows a needleless hub approaching a new type of the disinfecting luer connector according to an embodiment.
Figure 3B:
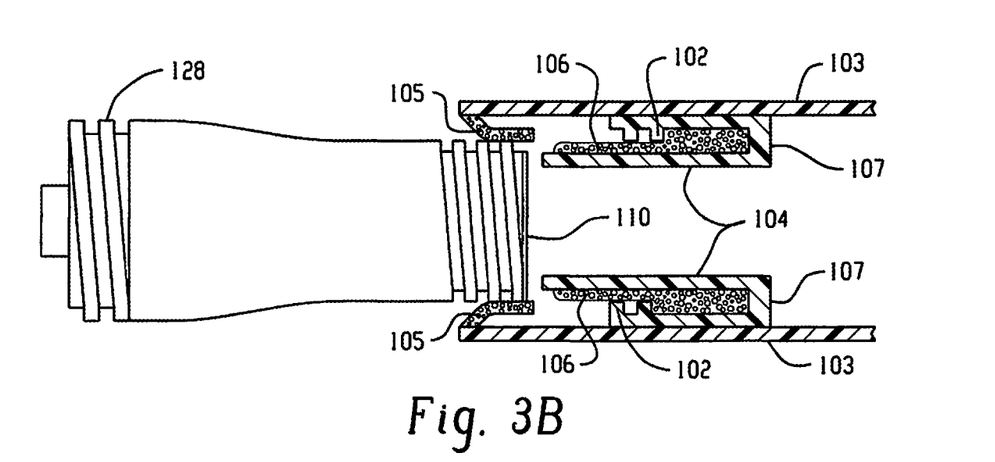
FIG. 3B shows a needleless hub penetrating half-way through the open proximal end of the receiving portion of the luer connector, according to an embodiment, to make a connection with the male luer threads thereof, after the first disinfecting pad has cleaned the injection membrane of the hub.

FIG. 3A shows a typical needleless hub with its proximal end coming into contact with a first embodiment of the invention, which is a disinfecting luer lock connector. This embodiment of the invention may engage a sterile needle, triple lumen catheter, a proximal end of the needleless hub connector, and other devices. The top portion of the hub has the injection membrane 110, a rigid rim disposed around it, and the female luer threads 101. The injection membrane 110 of the hub contacts the first disinfecting pad 105 impregnated with the disinfecting agent, which cleans and sterilizes the injection membrane. The first disinfecting member (pad) 105 adheres to the internal (side) wall 103 of the chamber 125. The second disinfecting member (pad) 106 is connected to the floor 107 of the chamber 125 and is situated between the male luer threads 102 and the syringe tip 104. Both disinfecting pads 105 and 106 are impregnated with a disinfecting agent such as povidone iodine, alcohol, chlorhexidine, etc., or any combination that provides antiseptic, antibacterial, and/or antiviral properties. Both disinfecting pads 105 and 106 are elastic enough so that they can bend out of the way and subsequently return to their original shape after the disinfecting pads 105 and 106 are no longer compressed. The side wall 103 can be made as only one wall which extends from the chamber's floor 107 all the way to the first disinfecting pad 105 or can be made as an extension of a shorter (secondary) side wall present on typical luer lock syringes. For better understanding, the side wall is shown as two walls, a shorter side wall, which can be found in all syringes, and a new extended wall, which completely covers the tip 104 of the syringe, thereby serving as a base for the first disinfecting pad 105 to connect. FIG. 3B illustrates a needleless hub shown half-way to making a connection with the syringe tip 104 of the invention. The central part of the first disinfecting pad 105 has an opening (for example, a cut) to allow the top portion of the hub to penetrate the first pad and to make a connection. The opening can be cut as a single line 112, or more than one line perpendicular to each other. The hub's injection membrane 110 has already penetrated the first disinfecting pad 105 and is now clean and sterilized. At this stage, the first disinfecting pad 105 is contacting and cleaning the female luer threads 101 of the hub. During penetration, the first disinfecting pad 105 is compressed, and the disinfecting agent is released to contact the injection membrane 110 and the female luer threads 101 of the hub.

The chamber 125 should be long enough so that the first disinfecting pad 105 has enough room to bend and not get caught in between the syringe tip 104 and the injection membrane 110. At the same time, the chamber 125 cannot be too long to cover a vent hole present on the body of some hubs. The second disinfecting pad 106 is shown in its resting position between the male luer threads 102 and the syringe tip 104.

Figure 4A:
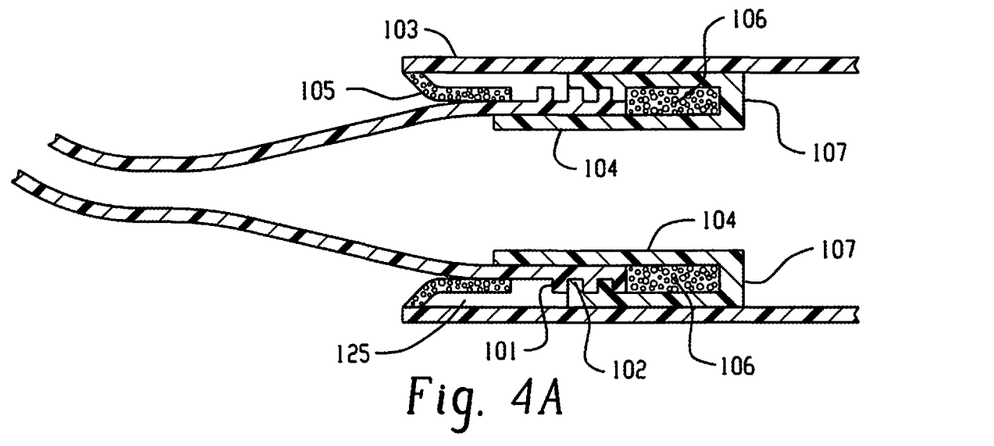
FIG. 4A shows one port of a typical triple lumen catheter making a complete connection with the disinfecting luer connector, according to an embodiment.
Figure 4B:
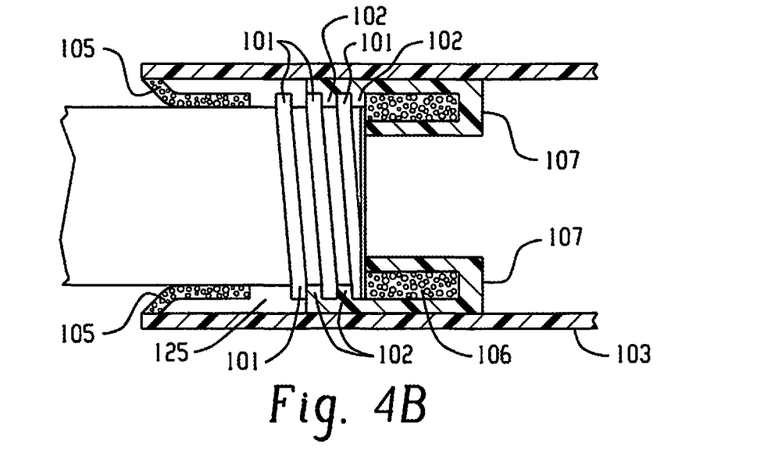
FIG. 4B shows a typical needleless hub making a complete connection with the disinfecting luer connector, according to an embodiment.
Figure 4C:
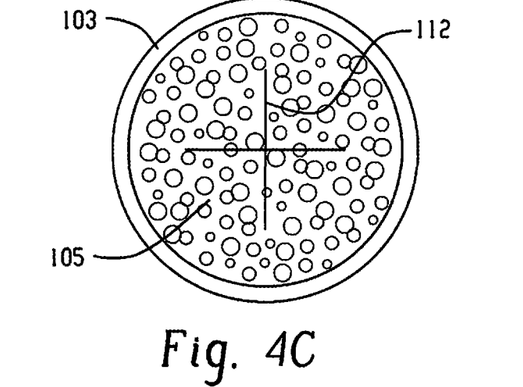
FIG. 4C is a view of the first disinfecting pad of the disinfecting luer connector, according to an embodiment, seen from the outside and the chamber's side wall disposed around the first disinfecting pad.
Figure 4D:
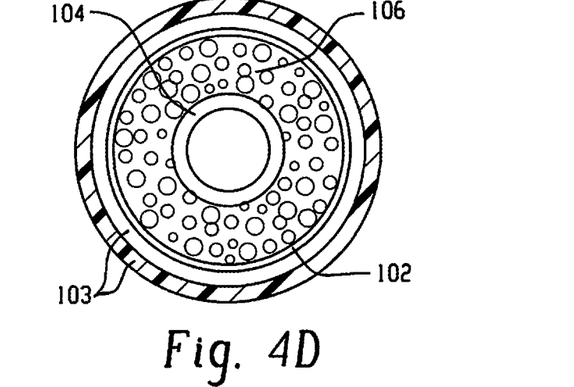
FIG. 4D is a cross-sectional view of the chamber of the disinfecting luer connector, according to an embodiment, at the level of the male luer threads.

FIG. 4A shows one port 123 of the triple lumen catheter making a complete connection with the device, according to the embodiment (disinfecting luer lock connector). As previously mentioned, the proximal end of this port has the female luer threads 101 but no injection membrane like a needleless hub. The port of the triple lumen catheter penetrates the first disinfecting pad 105 with its rim, and during the penetration, the rim is being sterilized. As the port of the triple lumen catheter advances, the female luer threads 101 of the port are being cleaned and sterilized with the first disinfecting pad 105. As the port of the triple lumen catheter advances even further, the rim pushes the second disinfecting pad 106 down and makes a complete connection with the syringe tip 104. The male luer threads 102 of the device and the female threads 101 of the port complement each other. The second disinfecting pad 106 is impregnated with the disinfecting agent, and compression of the second disinfecting pad 106 with the port's rim causes the disinfecting agent to release and sterilize the entire connection. The second disinfecting pad 106 is affixed to the floor 107 of the chamber 125. After the port and the disinfecting luer connector are disconnected, the second disinfecting pad 106 expands and absorbs an extra amount of the disinfecting agent. Both disinfecting pads 105 and 106 may be manufactured from various materials having good absorption ability. The disinfecting pads 105 and 106 should be sufficiently elastic so that they can bend out of the way and easily return to their original shapes. FIG. 4B is a picture of a needleless hub making a complete connection with the invention. At this stage, the injection membrane 110 penetrates the first disinfecting pad 105 and becomes sterilized together with the female luer threads 101 on the hub. The syringe tip 104 has pushed the injection membrane 110 inside and is ready for injection of the medication. The hub's rim 111 pushes the second disinfecting pad 106 down and causes the disinfecting agent to spread inside the chamber 125 and to sterilize all elements of this connection. FIG. 4C is a view of the first disinfecting pad 105 from the outside. It is shown here with the two central cuts 112 perpendicular to each other, which allow the top portion of the hub to penetrate the first disinfecting pad 105. It is noted that one cut might be enough to allow for penetration, however, more than two cuts may be present too. Around the first disinfecting pad 105 is the side wall 103 of the chamber 125 to which the pad is affixed. FIG. 4D is a cross-sectional view of the chamber 125 at the level of the male luer threads 102. It shows the longer (extended) side wall 103 first, then—the shorter side wall of a typical syringe. Although the shorter side wall may be optional and the male luer threads 102 may be affixed to only the longer side wall, the extended side wall may stretch from the chamber floor 107 all the way to the first disinfecting pad 105. Located next to the side wall are male luer threads 102, the second disinfecting pad 106, and the centrally located tip 104, which is used for injection.

Figure 5A:
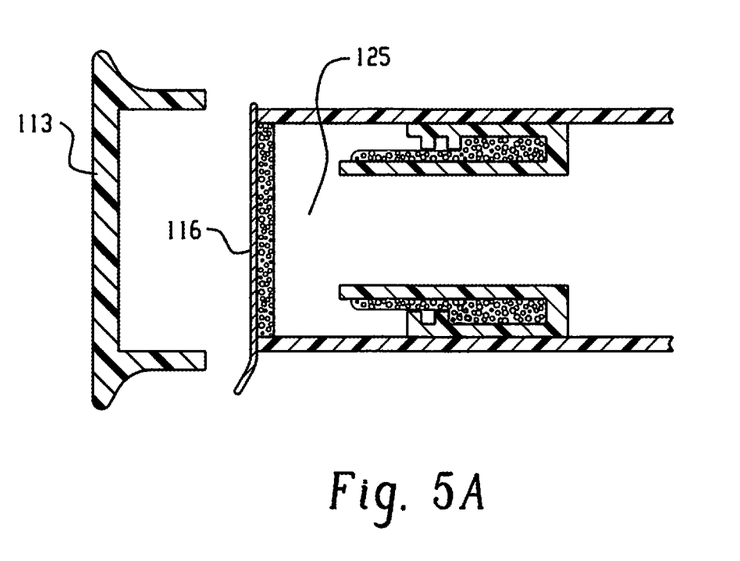
FIG. 5A shows the disinfecting pad of the disinfecting luer connector, according to an embodiment, protected with a peelable foil and ready for its first use, and also shows a protective cap which would cover the first disinfecting pad after each use.
Figure 5B:
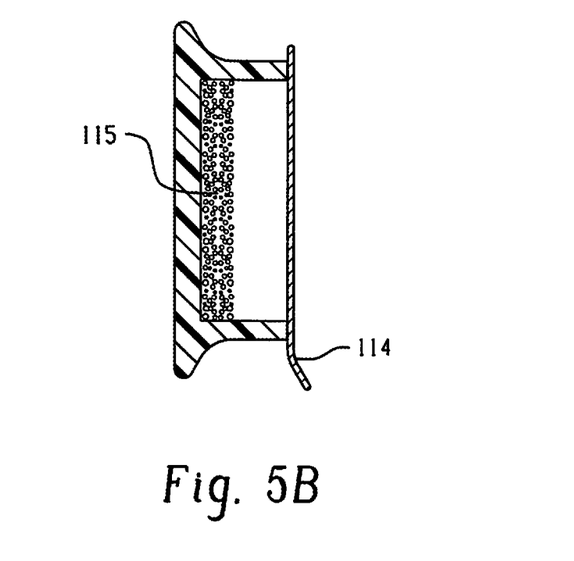
FIG. 5B shows another embodiment of the protective cap, which has a disinfecting pad inside the cap and a peelable foil to be removed before the first use of the protective cap.

FIG. 5A shows the first embodiment of the invention before its first use. The device, according to the embodiment, should come in a sterile, sealed package with a peelable foil 116 (or a plastic film) covering the first disinfecting pad 105. The foil represents a fluid barrier and prevents evaporation and spillage of the disinfecting agent. A medical provider would peel off the foil before the first use, and then connect the device with the hub or an intravenous catheter. After the injection is completed, a medical provider would disconnect the device (disinfecting luer connector) and place a protective cap 113 on it to keep it clean and prevent evaporation and spillage of the disinfecting agent. In this view, the protective cap should be included in the same sterile, sealed package with the disinfecting luer connector. FIG. 5B is a view of a more advanced form of the protective cap, which contains its own disinfecting pad 115 impregnated with the disinfecting agent and its own peelable foil 114 to prevent evaporation and spillage of the disinfecting agent. A medical provider is expected to remove the foil 114 before the first use. This extra disinfecting pad 115 located inside the protective cap would help keep the outer surface of the first disinfecting pad 115 from drying out. A small amount of the disinfecting agent may be disposed outside of both the first and second disinfecting pads 105 and 106 and may be free flowing inside the chamber. The sterilization technique needs to be carefully chosen for this sterile, sealed package to avoid evaporation or alteration of the disinfecting agent inside the device.

Figure 6A:
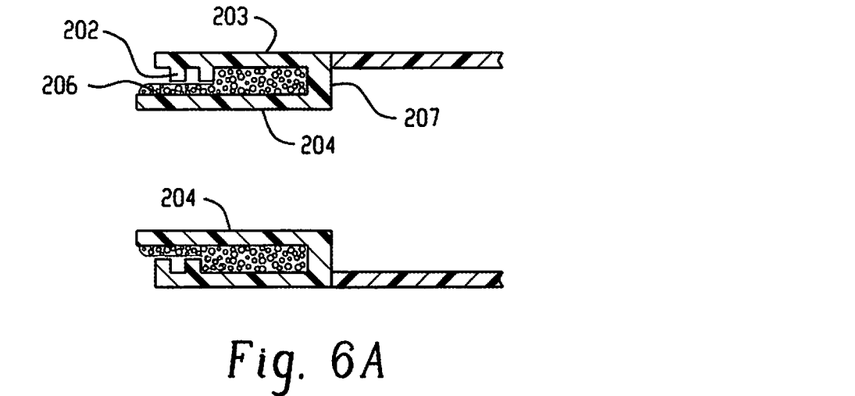
FIG. 6A shows another embodiment of the disinfecting luer connector, wherein only the second disinfecting pad is added to the typical luer lock connector.
Figure 6B:
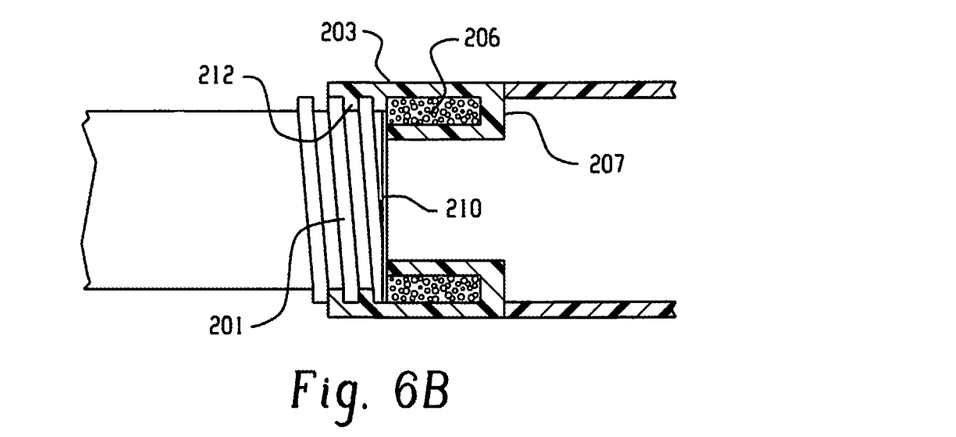
FIG. 6B shows another embodiment of the disinfecting luer connector, which is connected to the needleless hub.
Figure 6C:
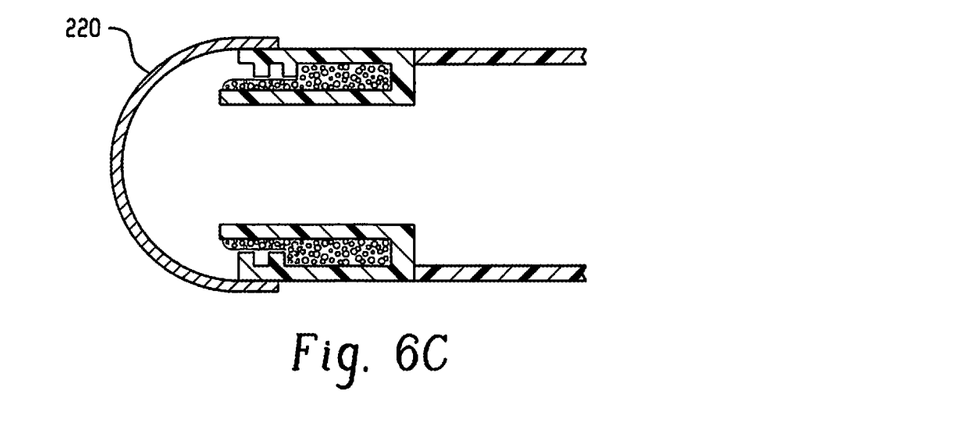
FIG. 6C shows the second embodiment of the disinfecting luer connector, covered with a protective cap after being used.

FIGS. 6A to 6B show a second embodiment of the invention. As shown in FIG. 6A, this form involves adding a second disinfecting pad 206 to a typical luer lock connector. The luer lock connector shown in FIG. 6A further has male luer threads 202, a side wall 203, and a floor wall 207. It is a simpler and less costly form of the invention, which is easy to manufacture. This embodiment would help decrease contamination of the connection made between the hub or the intravenous catheter with the male luer connector. FIG. 6B shows a complete connection made between the needleless hub and the second embodiment of the invention. The rim 211 of the hub pushes the disinfecting pad down to release the disinfecting agent, which cleans and sterilizes the top portion of the hub. Upon compression, the disinfecting pad 206 releases the disinfecting agent, which impregnates the exposed elements of the connection. This form of the invention would also need to have a peelable foil (or a plastic film) disposed over the proximal (outside) end of the device to prevent evaporation and spillage of the disinfecting agent. The foil would also provide a visual indication that the seal is broken. As shown in FIG. 6C, the protective cap 220 should also be available to cover the second device after the first use. Since a portion of the tip 204 is located outside the chamber in a typical luer lock connector, the protective cap 220 would have to be more domed here than in the first embodiment of the invention. Also, in this embodiment, the protective cap 220 may have its own disinfecting pad inside (not shown) to help keep the tip 204 of the invention in contact with the disinfecting agent and to prevent evaporation and spillage of the disinfecting agent from the disinfecting pad 206 inside the chamber.

Figure 7:
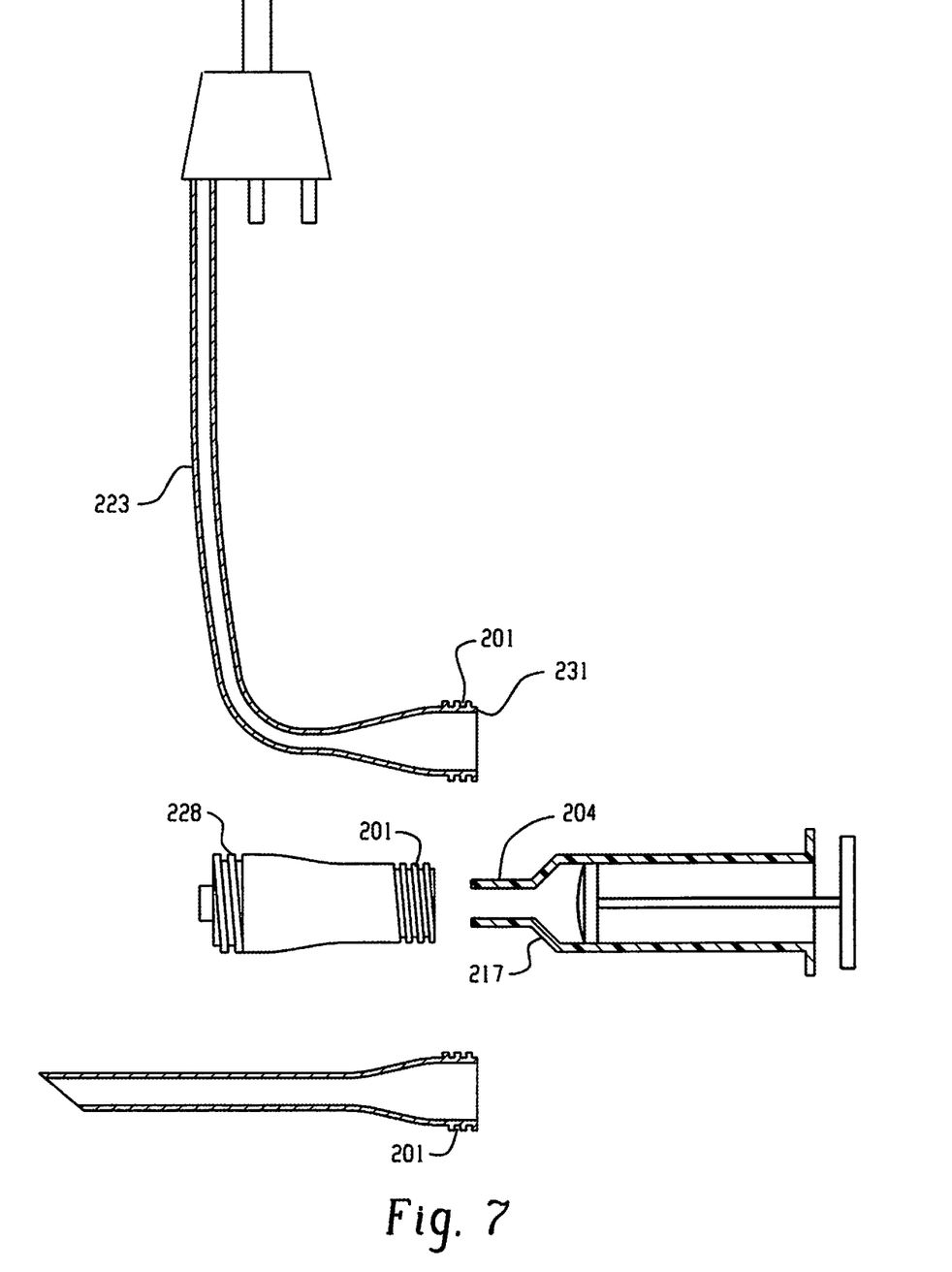
FIG. 7 shows a conventional triple lumen intravenous catheter (at the top left), a needleless hub connector (in the middle left), an intravenous needle (at the bottom left), and a typical luer slip syringe (in the middle right)

Similar to FIG. 1, on the left side, FIG. 7 shows a triple lumen catheter with only one port 223 of its three ports shown proximally, which has female luer threads 201 and an injection membrane 231, a needleless hub connector with the female luer threads 201 located on its proximal end and male luer threads 228 disposed on its distal end, and an intravenous needle with female luer threads 201. On the right side, FIG. 7 shows a typical luer slip syringe 217.

Figure 8:
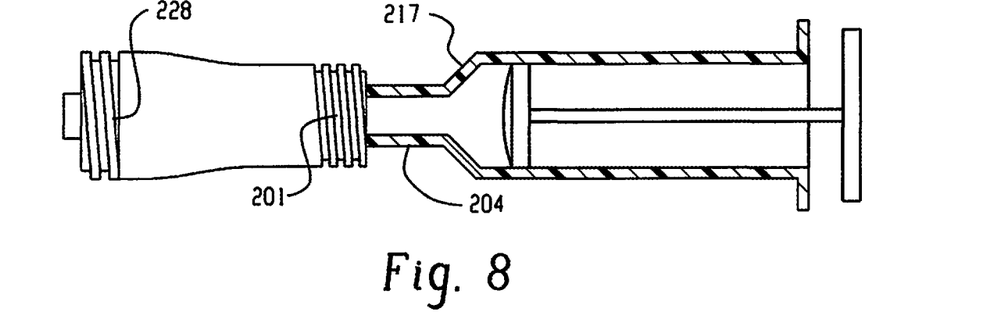
FIG. 8 shows a typical connection made by a typical needleless hub connector and a typical luer slip syringe.

FIG. 8 shows a typical luer slip syringe making a complete connection to the typical needleless hub connector. The tip 204 of the syringe slips inside the hub by pushing the injection membrane 210 of the hub down to provide a connection therebetween and to make the device ready for injection. A typical luer slip syringe or any other device having a luer slip connector does not have a chamber, threads, or a side wall.

Figure 9A:
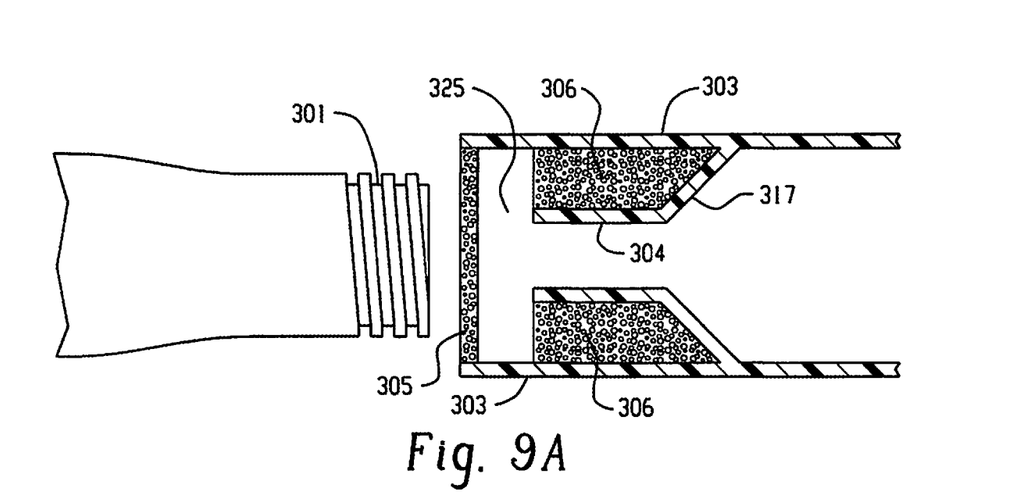
FIG. 9A shows a needleless hub connector approaching the first disinfecting pad of the disinfecting luer connector, according to another embodiment, with the luer slip instead of the luer lock connector.
Figure 9B:
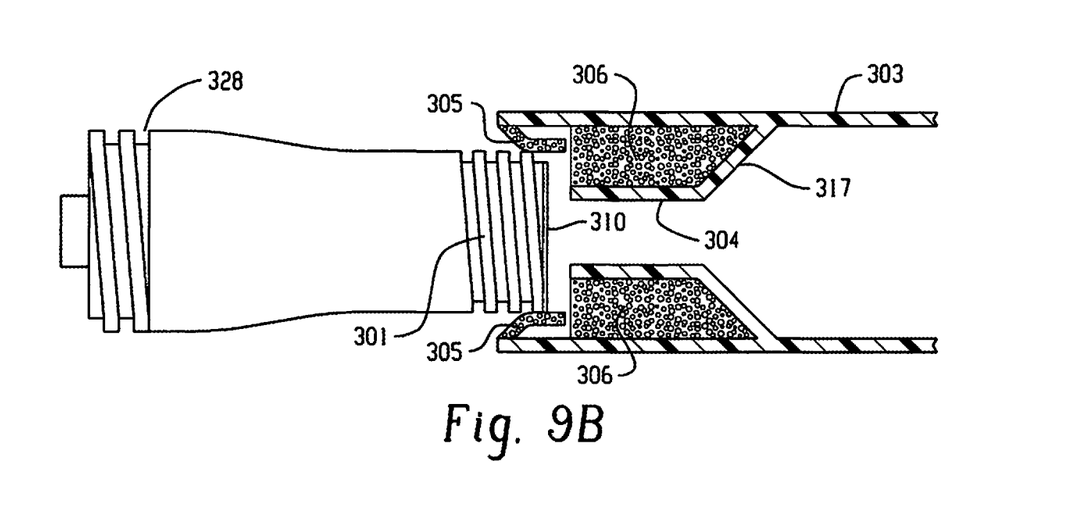
FIG. 9B shows a needleless hub penetrating the first disinfecting pad of the disinfecting luer connector, according to another embodiment, and approaching the syringe tip to make a complete connection.

FIG. 9A shows a typical needleless hub with its proximal end coming into close contact with a third embodiment of the invention which is a disinfecting luer slip connector. This form of the invention may be found on syringes and some other devices. The injection membrane 310 of the hub contacts the first disinfecting pad 305 impregnated with the disinfecting agent, which cleans and sterilizes the membrane 310. The first disinfecting pad 305 adheres to the side wall 303 of the chamber 325. In this embodiment, the second disinfecting pad 306 is connected not to the floor, as in the first embodiment of invention, but to the side wall 303 of the chamber 325, and is situated between the side wall 303 and the tip 304. The side wall 303 extends from the chamber floor 317 all the way to the first disinfecting pad 305. The chamber floor is shown to be angulated, but may also be flat, as in the first embodiment of the invention. In FIG. 9B, the needleless hub with male luer threads 328 disposed on its distal end is shown half-way to making a connection with the tip 304 of the invention. The central part of the first disinfecting pad 305 has an opening to allow the top portion of the hub to penetrate the first disinfecting pad 305 and to make a connection. The opening can be cut as a single line 312 or more than one line. When more than one line is present, the lines may be perpendicular to each other. The hub's injection membrane 310 has already penetrated the first disinfecting pad 305 and is now clean and sterilized. At this stage, the first disinfecting pad 305 is contacting and cleaning the female luer threads 301 of the hub. During penetration, the first disinfecting pad 305 is compressed and the disinfecting agent is released onto the injection membrane 310 and the female luer threads 301. The chamber 325 should be long enough so that the first disinfecting pad 305 has enough space to bend and not get caught in between the tip 304 and the injection membrane 310. Also, the first disinfecting pad 305 cannot be too long to prevent covering a vent hole present on the body of some hubs. The second disinfecting pad 306 is shown in its resting position between the side wall 303 and the tip 304.

Figure 10A:
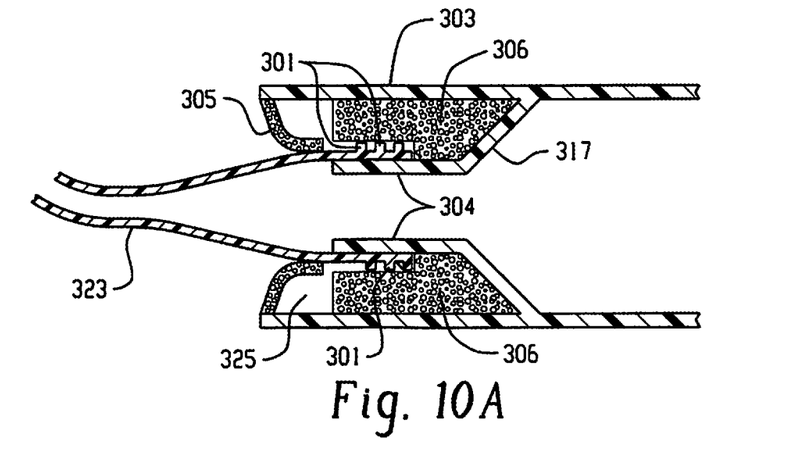
FIG. 10A shows one port of a typical triple lumen catheter making a complete connection with the disinfecting luer connector, according to another embodiment.
Figure 10B:
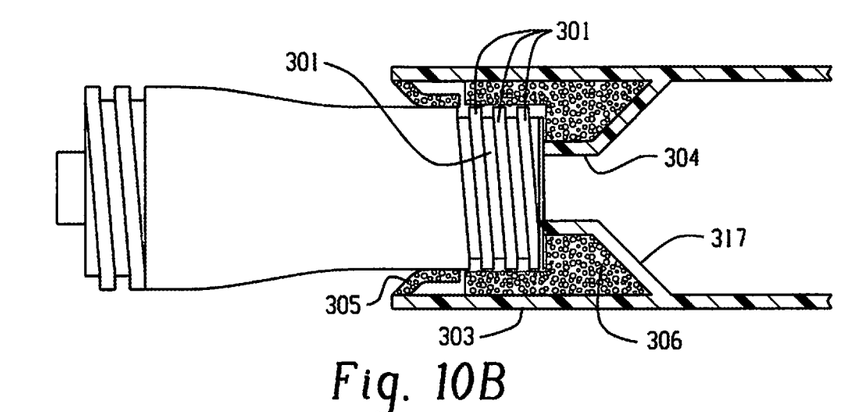
FIG. 10B shows a typical needleless hub making a complete connection with the disinfecting luer connector, according to another embodiment.
Figure 10C:
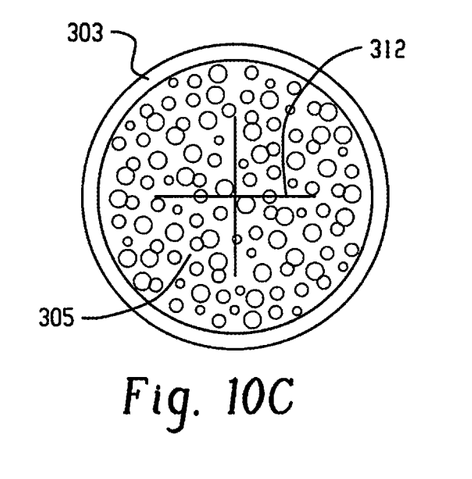
FIG. 10C is a view of the first disinfecting pad of the disinfecting luer connector, according to another embodiment, seen from the outside and the chamber's side wall disposed around it.
Figure 10D:
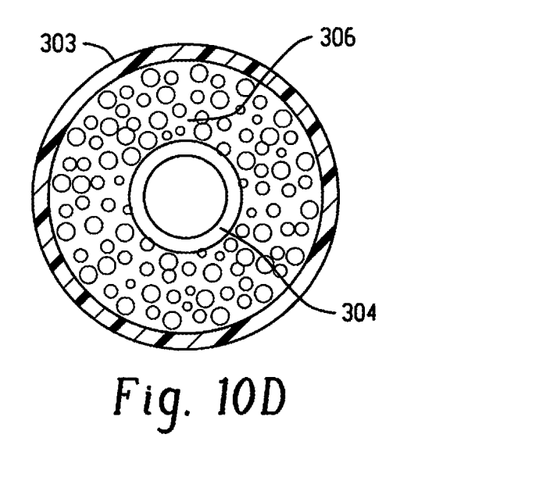
FIG. 10D is a cross-sectional view of the chamber of the disinfecting luer connector, according to another embodiment, at the level of the male luer threads.

FIG. 10A shows one port 323 of the triple lumen catheter making a complete connection with the third embodiment of the invention (disinfecting luer slip connector). As previously mentioned, the proximal end of this port has the female luer threads 301 but no injection membrane, like a needleless hub. The port of the triple lumen catheter penetrates the first disinfecting pad 305 with its rim to sterilize the rim. As it advances further, the female luer threads 301 of the port 323 are being cleaned with the first disinfecting pad 305. As it advances even further, the rim pushes the second disinfecting pad 306 down and aside while the tip 304 of the device enters the port 323 to make a connection. The second disinfecting pad 306 is impregnated with the disinfecting agent and the compression of the pad with the port's rim causes the disinfecting agent to be released and disinfect the connection. The second pad 306 is affixed to the side wall 303 of the chamber 325. After the port 323 and the disinfecting luer connector are disconnected, the second disinfecting pad 306 expands and absorbs an extra amount of the disinfecting agent. FIG. 10B shows the needleless hub making a complete connection with the device, according to this embodiment of the invention. At this stage, the injection membrane 310 and the female luer threads 301 on the hub penetrate the first disinfecting pad 305 and are sterilized. The tip 304 has pushed the injection membrane 310 inside and is ready for injection of a medication. The hub's rim 311 push the second disinfecting pad 306 down and aside to cause the disinfecting agent to spread inside the chamber 325 and disinfect all elements of this connection. Since the second disinfecting pad 306 in this third embodiment of the invention is pushed mostly aside toward the periphery and slightly down, it stays in close contact with the female luer threads 301 of the hub to clean the threads for the second time. FIG. 10C is a view of the first disinfecting pad 305 from the outside. Two central cuts 312 are shown perpendicular to each other to allow the top portion of the hub to penetrate the pad. One cut may be enough to allow for penetration, or more than two cuts may be made too. Around the first disinfecting pad 305 is the side wall 303 of the chamber 325 to which the disinfecting pad 305 is affixed. FIG. 10D is a cross-sectional view of the chamber 325 at the level of the second disinfecting pad 306, which shows the side wall 303, the tip 304, and the second disinfecting pad 306 disposed therebetween.

Figure 11A:
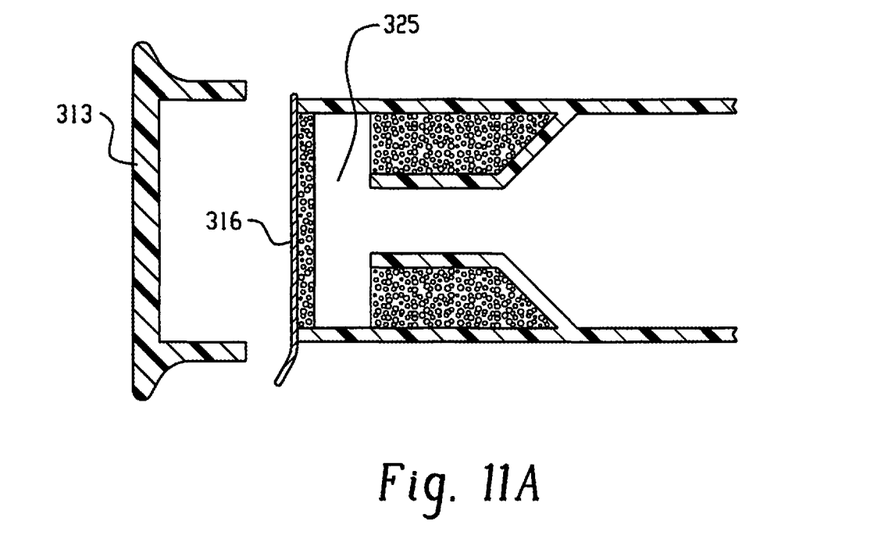
FIG. 11A shows another embodiment before the first use with its protective peelable foil and a protective cap sitting next to it.
Figure 11B:
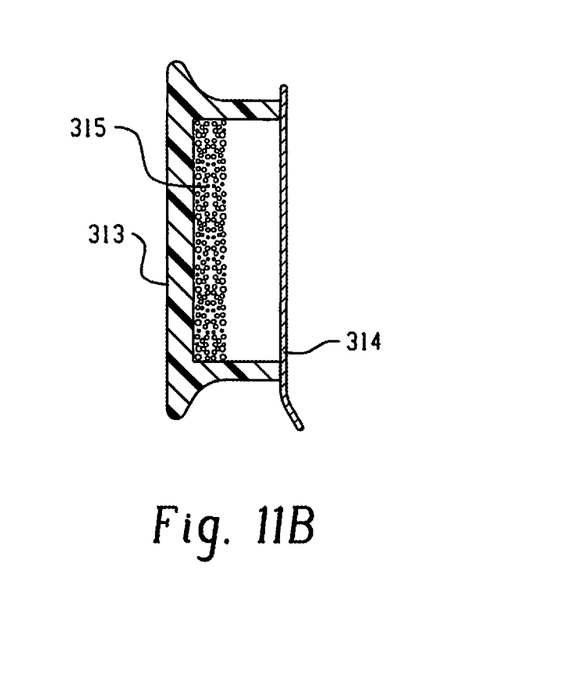
FIG. 11B is another variation of the protective cap having a disinfecting pad inside and a peelable foil protecting the disinfecting pad.

FIG. 11A shows the third embodiment of invention before its first use. The device should come in a sterile, sealed package with a protection, for example, a peelable foil 316 covering the first disinfecting pad 305. The foil represents a fluid barrier and prevents evaporation or spillage of the disinfecting agent. A medical provider would peel off the foil before the first use of the device, and then connect the device with the hub or an intravenous catheter. After the injection is completed, the medical provider would disconnect the device (disinfecting luer connector) and place a protective cap 313 on it to keep the device clean and to prevent evaporation and spillage of the disinfecting agent. In this view, the protective cap 313 should be included in the same sterile, sealed package with the disinfecting luer connector. FIG. 11B is a view of another embodiment of the protective cap, which contains its own disinfecting pad 315 impregnated with the disinfecting agent and its own peelable foil 314 to prevent evaporation and spillage of the disinfecting agent. A medical provider is expected to remove this foil 314 before the first use of the protective cap. This extra disinfecting pad 315 inside the protective cap 313 would help keep the outer surface of the first disinfecting pad 305 from drying out. A small amount of the disinfecting agent may be located outside of both the first 305 and second 306 disinfecting pads and may be free flowing inside the chamber 325. The sterilization technique has to be carefully chosen for this sterile, sealed package to avoid evaporation or alteration of the disinfecting agent inside the device.

Another embodiment provides a method for disinfecting a female port of a medical implement. The method includes providing an assembly for disinfecting a female port of a medical implement. The assembly includes a receiving portion and a disinfecting member disposed substantially inside the receiving portion. The receiving portion includes an open proximal end, a side wall, and a syringe tip. The side wall includes an internal surface defining a chamber for retaining a fluid into which the female port of the medical device is received. The internal surface has a plurality of protrusions disposed near the open proximal end, wherein the protrusions are shaped to engage helical threads of the female port of a medical implement. The syringe tip includes a passageway therethrough in a fluid communication with the chamber. The syringe tip further includes an external surface extending towards the open proximal end of the receiving portion of the assembly so as to create a cavity between the internal surface of the side wall and the external surface of the syringe tip. The disinfecting member is disposed near the open proximal end of the receiving portion in a direction substantially perpendicular to the internal surface of the side wall so as to completely cover the open proximal end. The disinfecting member has an opening to receive the female port of the medical implement. The disinfecting member is disposed substantially inside the cavity created by the protrusions of the internal surface of the side wall and the external surface of the syringe tip. The method further includes inserting the medical implement through the opening in the first disinfecting member inside the receiving portion of the assembly and connecting the female port of the medical implement by engaging the helical threads of the female port with the protrusions of the internal surface of the side wall.

The receiving portion may further include an additional disinfecting member disposed near the open proximal end of the receiving portion in a direction substantially perpendicular to the internal surface of the side wall so as to completely cover the open proximal end. The additional disinfecting member may include an opening to receive the female port of the medical implement.

The method may further include injecting a fluid through the female port of the medical implement into the receiving portion of the assembly. The female port of the medical implement may then be disconnected from the receiving portion of the assembly by disengaging the helical threads of the female port with the protrusions of the internal surface of the side wall. The medical implement may then be removed from the receiving portion of the assembly, and the open proximal end of the receiving portion may then be capped with a protective member.

The present inventive concept has been described in terms of exemplary principles and embodiments, but those skilled in the art will recognize that variations may be made and equivalents substituted for what is described without departing from the scope and spirit of the disclosure as defined by the following claims.

What is claimed is:

1. A syringe assembly for disinfecting a female port of a medical implement, the syringe assembly comprising:
   a receiving portion comprising
      an open proximal end;
      an open distal end;
      an external side wall comprising an internal surface defining a chamber for retaining a fluid into which the female port of the medical device is received, wherein the internal surface comprises a plurality of protrusions disposed on the internal surface of the external side wall and near the open proximal end of the receiving portion, wherein the protrusions are shaped to engage helical threads of the female port of the medical implement, and a non-threaded portion disposed between the plurality of protrusions and the open proximal end of the receiving portion; and
   a syringe tip disposed completely inside the chamber between the open proximal end of the receiving portion and the distal end thereof, wherein the syringe tip extends towards the open proximal end of the receiving portion, wherein the syringe tip comprises a passageway therethrough to provide a fluid communication within the chamber, wherein the syringe tip comprises an external surface facing the internal surface of the external side wall, and wherein the syringe tip is attached to the internal surface of the external side wall so as to create a cavity defined by the internal surface of the external side wall and the external surface of the syringe tip,
   a first disinfecting member disposed near the open proximal end of the receiving portion in a direction substantially perpendicular to the internal surface of the external side wall so as to completely cover the open proximal end, wherein the first disinfecting member comprises an opening to receive the female port of the medical implement,
   wherein the first disinfecting member is configured to bend distally into the receiving portion without contacting the syringe tip when the female port of the medical implement is received through the opening, and
   a second disinfecting member disposed substantially inside the cavity created by the internal surface of the external side wall and the external surface of the syringe tip,
   wherein the second disinfecting member extends over the non-threaded portion of the internal surface,
   wherein each of the first disinfecting member and the second disinfecting member comprises absorbing material.

2. The syringe assembly according to claim 1, wherein the second disinfecting member is disposed on the external surface of the syringe tip.

3. The syringe assembly according to claim 1, wherein the second disinfecting member is disposed on the internal surface of the external side wall.

4. The syringe assembly according to claim 1, wherein the female port of a medical implement comprises female luer threads, a rim, and optionally, a membrane, and wherein, upon contact with the female luer threads, the rim, and the optional membrane, the first disinfecting member and/or the second disinfecting member releases a disinfecting agent onto the female luer threads, the rim, and the optional membrane.

5. The syringe assembly according to claim 1, wherein the second disinfecting member is attached to the open proximal end of the receiving portion of the syringe assembly.

6. The syringe assembly according to claim 1,
   wherein the first disinfecting member and/or the second disinfecting member compresses upon contact with the female port of the medical implement to release a disinfecting agent, and
   wherein the first disinfecting member and/or the second disinfecting member subsequently returns to its substantially original shape when the female port of the medical implement no longer contacts the first disinfecting member and/or the second disinfecting member.

7. The syringe assembly according to claim 1, wherein the receiving portion further comprises an internal side wall disposed between the internal surface of the external side wall of the receiving portion and the external surface of the syringe tip.

8. The syringe assembly according to claim 1, wherein the opening in the first disinfecting member is a single line opening or an opening formed by two substantially perpendicular lines.

9. The syringe assembly according to claim 1, wherein the medical implement is a needleless hub connector, a triple lumen catheter, or an intravenous needle.

10. The syringe assembly according to claim 1, wherein the syringe assembly further comprises a protecting member disposed outside the open proximal end of the receiving portion and in full contact with that end so as to protect the first disinfecting member when the syringe assembly is not in use.

11. The syringe assembly according to claim 10, wherein the protecting member comprises a metal foil or a plastic film.

12. The syringe assembly according to claim 10, wherein the protecting member is a cap comprising a housing for covering the open proximal end of the receiving portion of the syringe assembly, wherein the housing comprises an opening and a cavity comprising a surface.

13. The syringe assembly according to claim 12, further comprising a third disinfecting member disposed within the housing of the cap and attached to the surface thereof to protect and disinfect the open proximal end of the receiving portion of the syringe assembly.

14. The syringe assembly according to claim 1,
wherein the first disinfecting member is affixed to the receiving portion of the syringe assembly,
wherein the first disinfecting member further comprises an external surface facing the medical implement, and
wherein the first disinfecting member is configured to bend distally from its original position without contacting the syringe tip to bring the external surface of the bent first disinfecting member in contact with the female port of the medical implement when the female port of the medical implement is received through the opening.

15. The syringe assembly according to claim 1, wherein the first disinfecting member, the second disinfecting member, or both are impregnated with a disinfecting agent.

16. A method for disinfecting a female port of a medical implement, the method comprising:
providing a syringe assembly comprising
a receiving portion comprising
an open proximal end;
an open distal end;
an external side wall comprising an internal surface defining a chamber for retaining a fluid into which the female port of the medical device is received, wherein the internal surface comprises a plurality of protrusions disposed on the internal surface of the external side wall and near the open proximal end of the receiving portion, wherein the protrusions are shaped to engage helical threads of the female port of the medical implement, and a non-threaded portion disposed between the plurality of protrusions and the open proximal end of the receiving portion of the internal surface; and
a syringe tip disposed completely inside the chamber between the open proximal end of the receiving portion and the distal end thereof, wherein the syringe tip extends towards the open proximal end of the receiving portion, wherein the syringe tip comprises a passageway therethrough to provide a fluid communication within the chamber, wherein the syringe tip comprises an external surface facing the internal surface of the external side wall, and wherein the syringe tip is attached to the internal surface of the external side wall so as to create a cavity defined by the internal surface of the external side wall and the external surface of the syringe tip,
a first disinfecting member disposed near the open proximal end of the receiving portion in a direction substantially perpendicular to the internal surface of the external side wall so as to completely cover the open proximal end, wherein the first disinfecting member comprises an opening to receive the female port of the medical implement,
wherein the first disinfecting member is configured to bend distally into the receiving portion without contacting the syringe tip when the female port of the medical implement is received through the opening, and
a second disinfecting member disposed substantially inside the cavity created by the internal surface of the external side wall and the external surface of the syringe tip,
wherein the second disinfecting member extends over the non-threaded portion of the internal surface,
wherein each of the first disinfecting member and the second disinfecting member comprises absorbing material,
inserting the medical implement through the open proximal end inside the receiving portion of the syringe assembly, and
connecting the female port of the medical implement to the receiving portion of the syringe assembly by engaging the helical threads of the female port with the protrusions of the internal surface of the external side wall.

17. The method according to claim 16, further comprising:
injecting a fluid through the female port of the medical implement into the receiving portion of the syringe assembly,
disconnecting the female port of the medical implement from the receiving portion of the syringe assembly by disengaging the helical threads of the female port with the protrusions of the internal surface of the external side wall,
removing the medical implement from the receiving portion of the syringe assembly, and
capping the open proximal end of the receiving portion with a protective member.

* * * * *